US006939359B2

United States Patent
Tu et al.

(10) Patent No.: US 6,939,359 B2
(45) Date of Patent: Sep. 6, 2005

(54) APPARATUS AND METHODS FOR VALVE REMOVAL

(75) Inventors: Hosheng Tu, Tustin, CA (US); Rodolfo C. Quijano, Laguna Hills, CA (US)

(73) Assignee: 3F Therapeutics, Inc., Lake Forest, CA (US)

( * ) Notice: Subject to any disclaimer, the term of this patent is extended or adjusted under 35 U.S.C. 154(b) by 133 days.

(21) Appl. No.: 10/375,718

(22) Filed: Feb. 26, 2003

(65) Prior Publication Data

US 2003/0216764 A1 Nov. 20, 2003

Related U.S. Application Data

(63) Continuation of application No. 09/861,727, filed on May 21, 2001, now abandoned.

(51) Int. Cl.[7] .......................... A61B 18/18; A61B 17/22; A61B 17/32
(52) U.S. Cl. .................. 606/159; 606/170; 606/37; 606/14
(58) Field of Search ................ 606/14, 37, 159, 606/170

(56) References Cited

U.S. PATENT DOCUMENTS 6,039,748 A * 3/2000 Savage et al. .............. 606/180

* cited by examiner

Primary Examiner—Glenn K. Dawson
Assistant Examiner—D. Jacob Davis
(74) Attorney, Agent, or Firm—Jones Day

(57) ABSTRACT

This invention discloses a medical catheter and methods for removing a defective valve from a patient endoluminally. The method may comprise inserting a medical catheter endoluminally to a site of the defective valve; deploying a coupling mechanism of said medical catheter to stabilize and immobilize a free edge of at least one valve leaflet; deploying a cutting mechanism of said medical catheter to cut a valve base of said defective valve; and removing said defective valve from the patient.

6 Claims, 10 Drawing Sheets

APPARATUS AND METHODS FOR VALVE REMOVAL

RELATED APPLICATION

This application is a continuation of application Ser. No. 09/861,727, filed May 21, 2001, now abandoned, the entirety of which is incorporated herein by reference.

BACKGROUND OF THE INVENTION

1. Field of the Invention

The present invention generally relates to medical apparatus and methods for valve removal from a patient. More particularly, the invention relates to an endoluminal catheter and methods for removing a defective valve and adapted for implantation of a valvular prosthesis.

2. Description of the Related Art

A valve in a body circulation system is to ensure unidirectional blood flow. When a valve is defective, a person feels weak and appears difficult to handle route physical workload or exercise. A defective valve may include a stenotic valve that can't open completely, a valve unable to close completely leading to regurgitation of blood back through the valve, or an infected valve. Other conditions leading to a defective valve may include changes in valve structure, rheumatic fever or other unknown reasons.

Defective cardiac valves have been routinely treated using an open-chest surgery for repair or replacement of aortic, mitral and other heart valves. Valves that are heavily calcified or significantly compromised by disease may need to be replaced. These procedures typically involve a full sternotomy and quadrangular resection of the anterior leaflet, while on cardiopulmonary bypass.

One emerging technique for valve replacement is a minimally invasive endoluminal procedure. This may be performed by a catheter-based percutaneous, endoscopic, or laparoscopic procedure. Before a valvular prosthesis can be implanted, the whole valve, including the valve base and its associated valve leaflets need to be removed from a patient.

Certain conventional surgical endoscopic, and laparoscopic procedures utilize staples or clips for repair of incisions or wounds, implantation of prostheses, anastomoses and the like. For example, surgical staples have been disclosed comprising angled and arcuate central and leg regions which can be flattened by a stapling tool having an anvil and driving structure. One such staple has been disclosed with side portions curved substantially in the form of an arc of a circle to prevent tearing of tissue by producing puncture channels.

Various forms of stapling tools have been disclosed. One such surgical instrument consists of an anvil adapted to lie flush with the skin, a cartridge containing a plurality of staples and a U-shaped pusher for bending the staples around the anvil. Such instruments typically have mechanical actuators within a handle mechanism for positioning the staples and activating the driver or pusher against the staple and anvil.

Laparoscopic procedures have also used staples, balloons and clip appliers or staple guns for procedures such as cholecystostomies, ligation and hernia repair. Laufer et al. in U.S. Pat. No. 6,149,660 discloses such systems for intraluminally repairing blood vessels of vein valves. The Laufer et al. patent discloses the minimally invasive system for intraluminal repair of a body organ, lumen or cavity, for example, a blood vessel or a vein valve, using a catheter based system for deploying a bendable clip appliance, the entire contents of which are incorporated herein by reference.

Kuehn et al. in U.S. Pat. No. 6,165,183 discloses a leaflet fastener applicator generally has a size allowing insertion through a catheter and is capable of holding portions of opposing heart valve leaflets. Kuehn et al. also refers to a valve repair technique of an edge-to-edge suturing of the mitral leaflets, commonly referred to as a "bow-tie" repair. The bow-tie repair generally involves the use of a centrally located suture, although a suture can be placed close to a commissure, or multiple sutures can be used to complete the repair. A centrally placed suture creates a double orifice valve, which resembles a bow-tie. The entire contents of Kuehn et al. patent are incorporated herein by reference.

Williamson, IV et al. in U.S. Pat. No. 6,162,233 discloses wire fasteners having legs with lengths that are used to secure items, such as prosthesis valves to a patient during minimally invasive surgery. The fasteners are manipulated, tensioned and formed from the leg end of the fasteners and tools for initially placing the fasteners and for immobilizing, tensioning, cutting and bending the fasteners legs are disclosed. The entire contents of Williamson, IV et al. patent are incorporated herein by reference.

Stevens et al. in U.S. Pat. No. 6,125,852 and Donlon et al. in U.S. Pat. No. 6,010,531 disclose a minimally invasive device and methods for heart valve surgery, the entire contents of which are incorporated herein by reference. The surgical intervention may comprise replacing the cardiac valve with a prosthetic valve, wherein the native valve is removed using a tissue removal instrument.

Hamblin, Jr. et al. in U.S. Pat. No. 6,033,419 discloses an apparatus for cutting a heart valve annulus, the entire contents of which are incorporated herein by reference. The disadvantage of Hamblin, Jr. apparatus is that without immobilizing and stabilizing the valve leaflets, the apparatus may swing or float within the blood flow due to systolic and diastolic flows. Therefore, it is difficult to target the anatomic site of the valve structure remotely and cut the heart valve base effective for implantation of a prosthetic valve.

The above-mentioned patents disclose methods for fastening the leaflets or methods of removing a native valve using a tissue removal instrument, or methods for repairing a heart valve. However, no prior art has disclosed an endoluminal catheter generally having suitable dimensions for deployment and insertion into a human cardiovascular system in the vicinity of a defective valve by immobilizing the valve leaflets, separating a valve base of the defective valve, and removing said defective valve.

Therefore, it is an object of the present invention to overcome the disadvantages of the prior art and provide an improved apparatus and methods for removing a defective valve, wherein the removed annular space is suitable with implantation of a replacement valve.

SUMMARY OF THE INVENTION

In general, it is an object of the present invention to provide a method and an improved apparatus for removing a defective valve from a patient, the method comprising immobilizing valve leaflets of the defective valve, separating a valve base from a valve root of the defective valve, wherein the valve base comprises at least one commissure, and thereafter removing the defective valve from the patient. The valve base to be removed is configured to yield suitable dimensions so as the annular space is effective for implantation of a replacement valve, such as a mechanical valve, a biological valve, or a valved conduit. The method may be performed by an endoluminal, laparoscopic, and/or percutaneous procedure.

In a preferred embodiment, the method comprises the step of immobilizing the valve leaflets by clamping a free edge of the at least one valve leaflet using a coupling mechanism of an endoluminal catheter, wherein the catheter also has a cutting mechanism for separating the valve base from the valve root of the defective valve. The cutting mechanism is preferably located at a distal section of the endoluminal catheter and configured to be at a predetermined position relative to the coupling mechanism. The relative position of the coupling mechanism and the cutting mechanism of the catheter is to facilitate precise separation of the valve base from the valve root and create a suitable annular space for valve implantation.

Further, the cutting mechanism may be a sharp-edge element configured to separate the valve base from the valve root of the defective valve. A radiofrequency source may be coupled to the sharp-edge element configured for heating and cutting the valve base. In an alternate embodiment, the cutting mechanism may be a fiber optic laser element configured to separate the valve base from the valve root of the defective valve.

The defective valves to be removed in the present invention may include, but not limited to, mitral valves, aortic valves, pulmonary valves, tricuspid valves, venous valves and the like.

It is another object of the present invention to provide a medical catheter for removing a defective valve from a patient comprising an elongate catheter shaft having a catheter distal end, a catheter distal section, a catheter proximal end, and at least a lumen between the catheter distal end and the catheter proximal end; a deployable inner catheter located within one of the at least one lumen; a coupling mechanism located at the catheter distal section, wherein the coupling mechanism is configured to couple, grip and immobilize a free edge of the at least one valve leaflet of the defective valve; and a cutting mechanism mounted at a distal end of the deployable inner catheter configured to cut and separate a valve base of the defective valve from a valve root of the defective valve.

The coupling mechanism of the medical catheter may further comprise a stapling element configured to couple each free edge of the valve leaflets onto said stapling element. Alternately, the coupling mechanism may comprise a gripping element or a gluing element configured to couple each free edge of the valve leaflets onto the gripping element or the gluing element, respectively. Other coupling mechanism, such as with clips, fasteners or suction, may also be applicable.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF THE PREFERRED EMBODIMENT

Referring to FIGS. 1 to 6, what is shown is an embodiment of the medical catheter system, comprising a coupling mechanism for coupling, immobilizing, and stabilizing the free edge of at least one valve leaflet and a cutting mechanism to separate the valve base from the defective valve adapted for replacement of a prosthetic valve or a cryopreserved autologous valve.

To provide consistency with the common usage of terms used in the present invention and in medical surgery arts, the term "valve base" in this invention refers to any tissue surrounding the valvular structure so that, upon removal of the valve base, an annular space is configured having suitable dimension and defined effective for implantation of a replacement valvular prosthesis. In the example of mitral or tricuspid valves, the valve base may refer to the continuum mechanism that consists of myocardium, papillary muscles, chordae tendinae and commissures. In the example of the aortic valves, the valve base may refer to the commissures and its associated tissue at the valvular annulus. However, the valve base may not include the aortic root, unless the aortic root is aneurysmal or totally dilated that needs removal. In the example of a venous valve, the valve base may refer to commissures and the tissue around the commissures. A combination of the valve base and its associated leaflets is the structure to be removed defined in the present invention.

Figure 1:
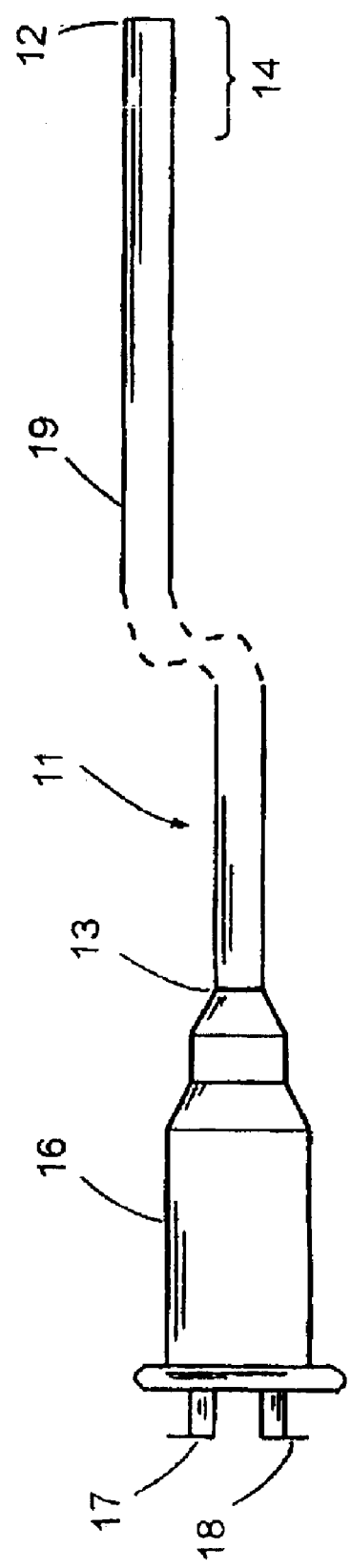
FIG. 1 is an overall view of a medical catheter for valve removal constructed in accordance with the principles of the present invention.

FIG. 1 shows an overall view of a medical catheter for valve removal constructed in accordance to the principles of the present invention. The medical catheter 11 comprises a catheter shaft 19, a distal end 12, a proximal end 13, a distal section 14, and at least a lumen 21 between the distal end 12 and the proximal end 13. The catheter further comprises a handle 16 attached to the proximal end 13 of the catheter shaft 19. A cutting mechanism for separating the valve base from the valve root may be secured to a cutting deployment control 17 at the handle 16. Typically the cutting deployment control 17 is a push-pull or rotating mechanism which is well known to an ordinary artisan skilled in the art. Similarly, a coupling mechanism for coupling the free edge of a leaflet may be secured to a coupling deployment control 18 at the handle 16. A coupling mechanism may include a stapling element, a gripping element, a gluing element, and/or a suction element. Other coupling means for securely coupling the free edge of the leaflets to the appropriate catheter end is also applicable. The coupling mechanism of the present invention may be a temporary coupling of the leaflet with the catheter, such as a suction element. However, a permanent coupling or semi-permanent coupling is also applicable.

Valve removal may be performed by an open surgery procedure, a laparoscopic procedure, or a percutaneous procedure. To effectively cut the valve base and remove a defective valve, it is usually preferred to apply an endoluminal catheter from the outflow side toward the free edge of the leaflets so as to grip the free edge(s) by the coupling mechanism. Once at least one free edge of the leaflets is secured and coupled to the catheter, force may be exerted onto the cutting mechanism for enhanced separating the valve base from the valve root.

The catheter of the present invention may be made of any suitable biocompatible material such as polyurethane, silicone, polyimide, Nylon, polyester or the like. The construction material for the cutting mechanism may be a metallic material, a plastic, or rigid conductive non-metallic material that has strength, pushability and flexibility. The coupling mechanism may be made of any suitable biomaterial adapted for the intended use. Additional features to make the medical catheter better suit for the intended use are also included within the scope of the present invention. They may include irrigation, guidewire lumen, ultrasound guiding/imaging, and other means for ablating the tissue of the valve base.

Figure 2:
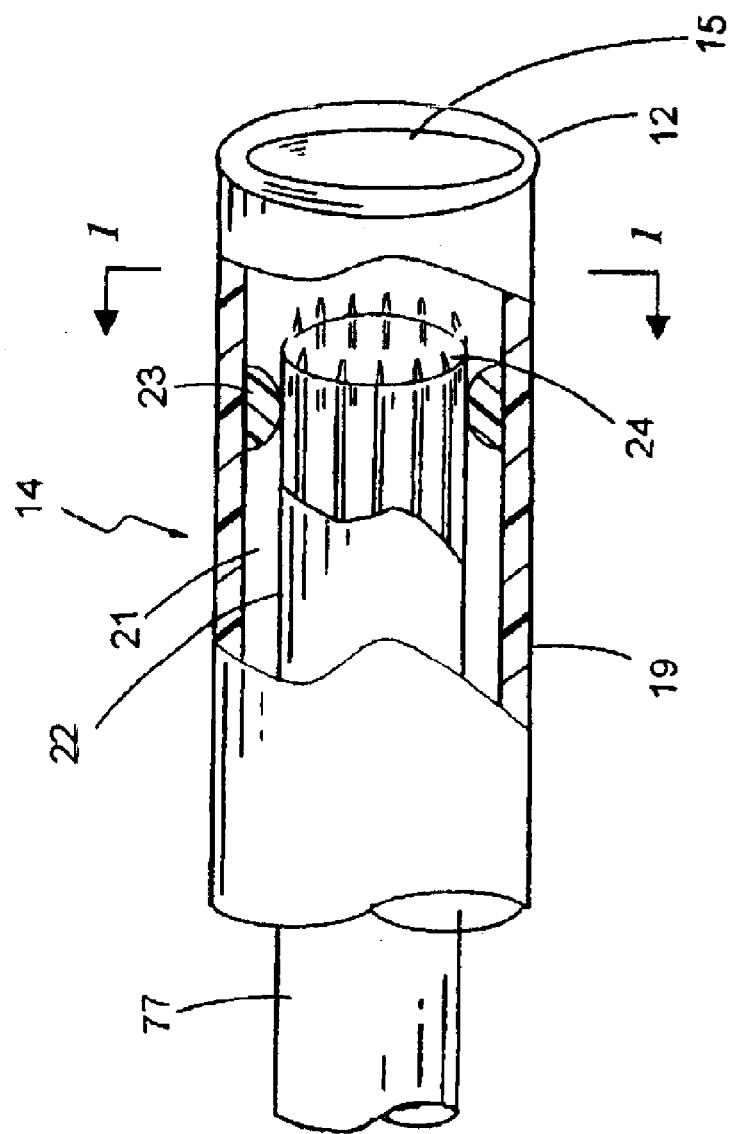
FIG. 2 is a cross-sectional view of the distal section of the medical catheter.

FIG. 2 shows a cross-sectional view of the distal section 14 of the medical catheter 11. There is at least an opening 15 at the distal end 12 of the catheter. A deployable inner catheter 77 is located within one of the at least one lumen 21, wherein a cutting mechanism 22 is attached to the distal end of the inner catheter and is located at the catheter distal section 14. The cutting mechanism 22 is configured to cut and separate a valve base of the defective valve from a valve root of the defective valve. The cutting mechanism may have a sharp-edge cutting element 24, a fiber optic laser element 28A, an ultrasonic ablation element, or other appropriate means for separating the valve base from the valve root. The proximal end of the deployable inner catheter is secured to the cutting deployment control 17. A coupling mechanism is located within the lumen of the cutting mechanism 22. The cutting mechanism and the coupling mechanism can be operated independently or controlled by a robot.

The sharp-edge cutting element 24 may comprise a hole-saw teeth or other configuration for cutting into the tissue. The sharp-edge cutting element may also be rotatable to enhance the cutting efficiency. Other mechanical, chemical, electrical or physical cutting means would also be applicable in the present prevention.

A circular supporting ring 23 may be located at the distal section 14 of the catheter shaft 19 between the inner wall of the catheter shaft and the outer surface of the cutting mechanism, wherein the supporting ring 23 or other appropriate means is adapted for supporting and guiding the distal portion of the cutting mechanism 22 at along the central axis of the catheter shaft 19.

Figure 3:
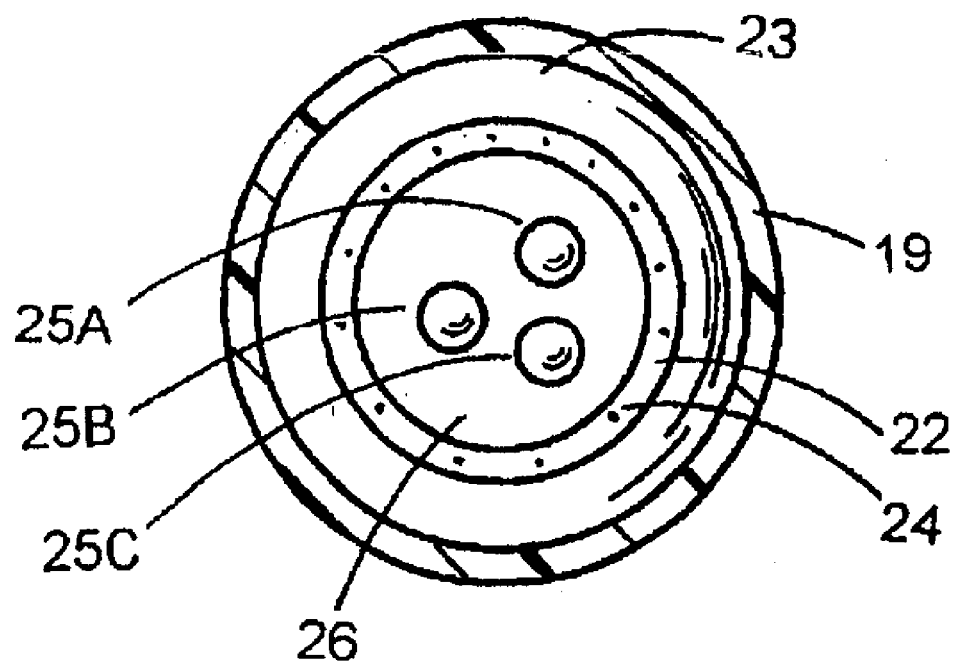
FIG. 3 is a transverse cross-sectional view of the distal section, section 1—1 of FIG. 2.

FIG. 3 shows a transverse cross-sectional view of the distal section 14, section 1—1 of FIG. 2, wherein a coupling mechanism comprises a plurality of members 25A, 25B, 25C in the form of a stapling element 31, a gripping element 42 or a gluing element 51.

The coupling mechanism is mounted at a distal section 14 of the catheter 11 and is deployably controlled by the coupling deployment control 18 at the handle 16, wherein the coupling mechanism is configured to grip and immobilize a free edge of at least one valve leaflet of the defective valve.

Figure 4A:
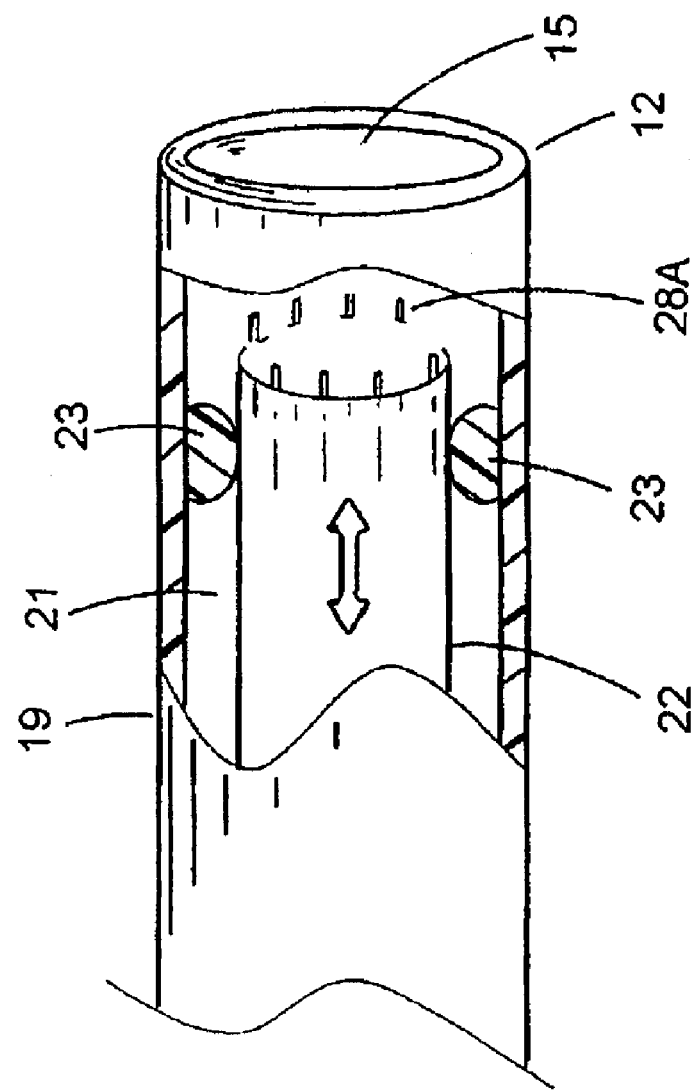
FIG. 4A is an illustrative view for deploying the cutting mechanism: Stage #1 showing the cutting mechanism retracted within the catheter shaft during the catheter insertion operation.
Figure 4B:
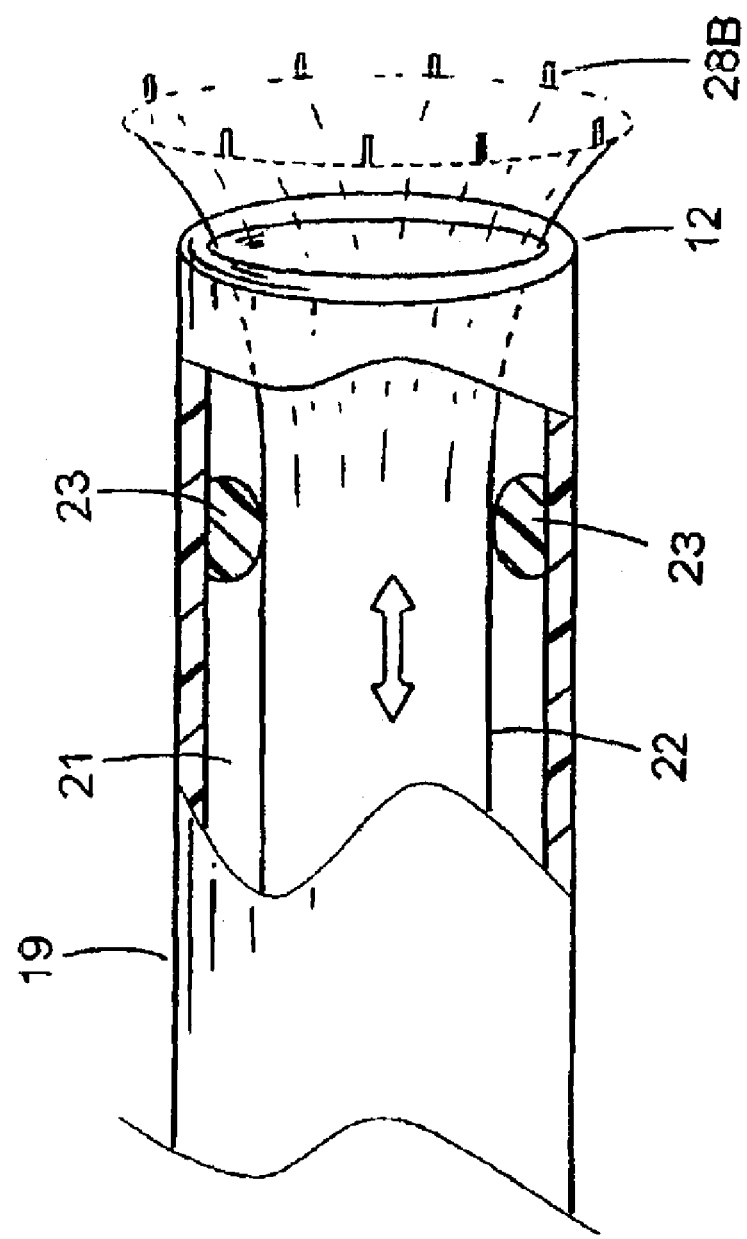
FIG. 4B is an illustrative view for deploying the cutting mechanism: Stage #2 showing the cutting mechanism in the process of deployment out of the catheter shaft.
Figure 4C:
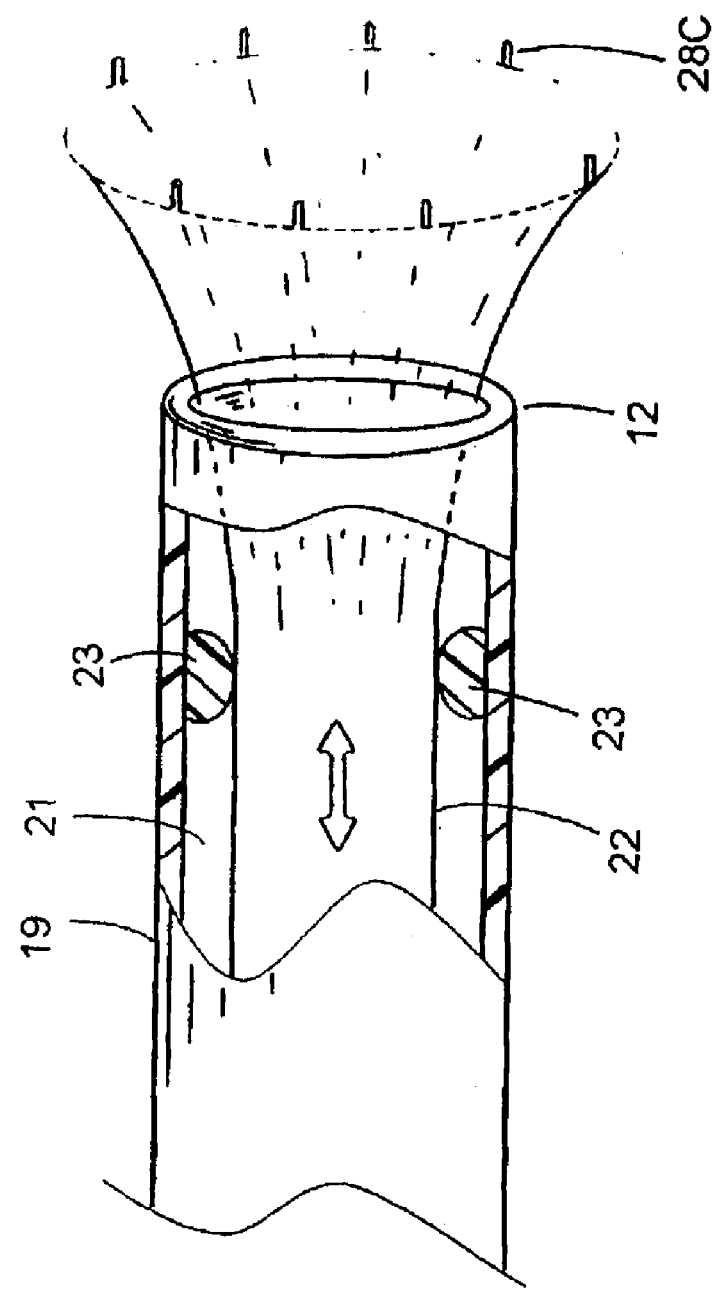
FIG. 4C is an illustrative view for deploying the cutting mechanism: Stage #3 showing the cutting mechanism fully deployed out of the catheter shaft.

FIGS. 4A–4C show an illustrative view for deploying the cutting mechanism in three consecutive stages. FIG. 4A shows the stage #1 cutting mechanism 22 that is retracted within the catheter shaft 19 during the catheter insertion or removing operation.

In one embodiment, a fiber optic laser element 28A is mounted at the very distal tip of the cutting mechanism 22. An external laser energy source is coupled to each of the laser optic fibers configured for cutting and separating the valve base from the valve root of the defective valve. The laser energy source may be supplied to one or more optic fibers simultaneously, sequentionally or in other desired operating mode. The cutting mechanism is deployable with a forward or backward movement by the cutting deployment control 17 at the handle 16.

FIG. 4B shows the stage #2 cutting mechanism 22 in the process of deployment out of the opening 15 of the catheter shaft 19. The fiber optic laser element 28B for the stage #2 may be self-expandable upon releasing from the constraint of the catheter shaft 19. The circumferential dimension of the expanded element 28B is adapted to cause the valve base being separated from the valve root. The circumferential shape, size and configuration of the fiber optic laser element 28B may be predetermined, pre-shaped, or designed accordingly.

If a larger circumferential space is needed to cut the adequate valve base, then the expandable fiber optic laser element 28C is to be deployed further as shown in FIG. 4C. FIG. 4C shows the stage #3 cutting mechanism 28C that is fully deployed out of the opening 15 of the catheter shaft 19. The cutting mechanism is deployable and retractable.

As discussed herein, there disclosed a method for removing a defective valve from a patient endoluminally, the method comprising several major steps of: (a) inserting a medical catheter endoluminally to a site of the defective valve; (b) deploying a coupling mechanism of the medical catheter to stabilize and immobilize a free edge of at least one valve leaflet; (c) deploying a cutting mechanism of the medical catheter to cut a valve base of the defective valve; and (d) removing the defective valve from the patient.

Figure 5A:
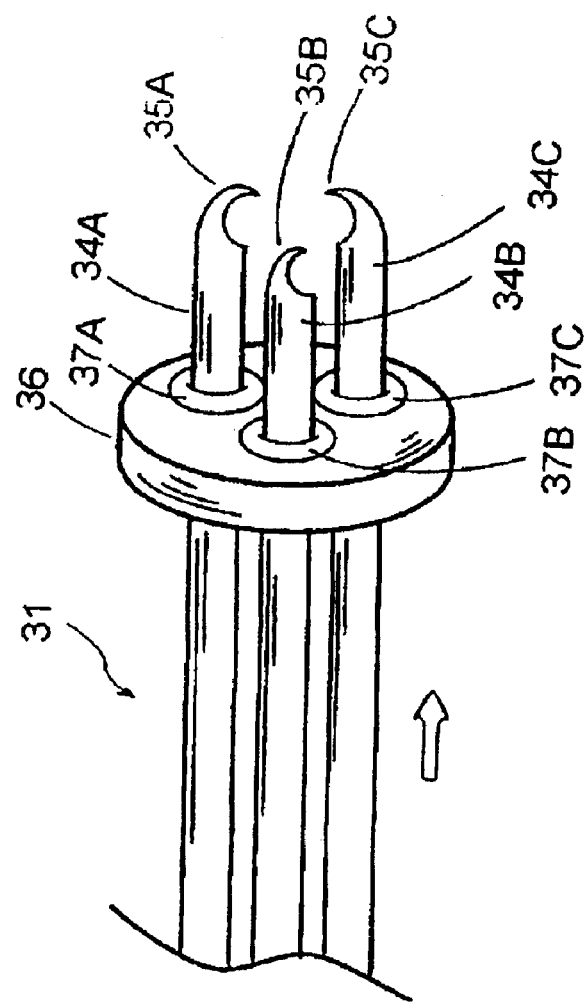
FIG. 5A is an embodiment of the coupling mechanism of the present invention comprising a stapling element for coupling the leaflets onto the medical catheter.

FIG. 5A shows an embodiment of the coupling mechanism of the present invention comprising a stapling element 31 with a plurality of stapling members 34A, 34B and 34C for coupling the one or more leaflets onto the medical catheter 11. In a preferred embodiment, each coupling member 34A, 34B or 34C passes through a restraining passageway 37A, 37B, or 37C of a restraining support 36, respectively. The restraining support 36 also serves as a supporting means for supporting the coupling members from drifting away off the central axis of the catheter shaft 19. The stapling members have staples 35A, 35B or 35C at the distal end for stapling the free edge of each leaflet onto each corresponding coupling staple member. The stapling mechanism and structure has been disclosed in U.S. Pat. No. 6,149,660, entire contents of which are incorporated herein by reference.

Figure 5B:
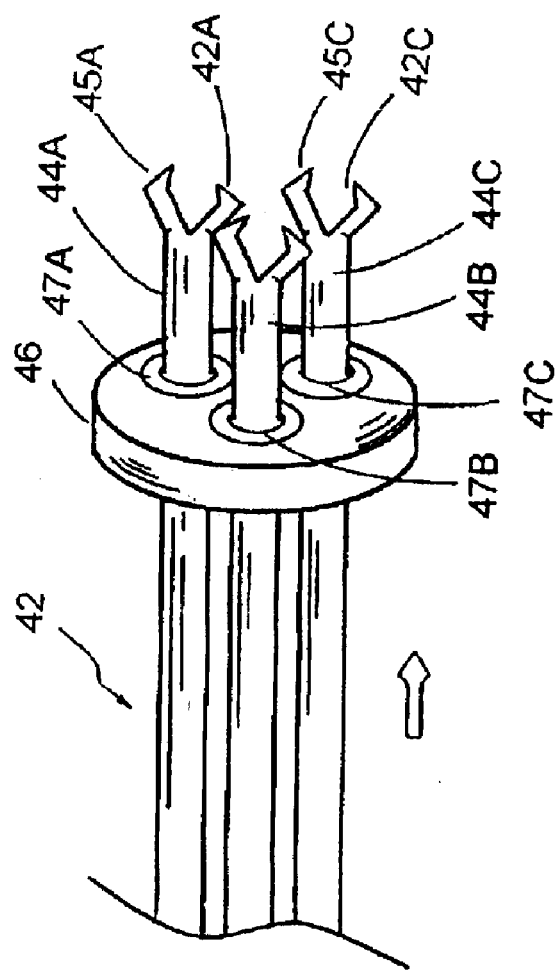
FIG. 5B is an embodiment of the coupling mechanism of the present invention comprising a gripping element for coupling the leaflets onto the medical catheter.

Similarly, FIG. 5B shows an embodiment of the coupling mechanism of the present invention comprising a gripping element 42 with a plurality of gripping members 44A, 44B and 44C for coupling the leaflets onto the medical catheter 11. As shown in FIG. 5B, each gripping member 44A, 44B or 44C passes through a restraining passageway 47A, 47B or 47C of a restraining support 46. Each gripping member 44A, 44B or 44C has a pair of gripping arms 45A/42A, 45B/42B, or 45C/42C at its distal end for gripping the free edge of each leaflet onto each corresponding gripping member. The gripping mechanism and methods has been disclosed in U.S. Pat. No. 5,885,238, entire contents of which are incorporated herein by reference.

Figure 5C:
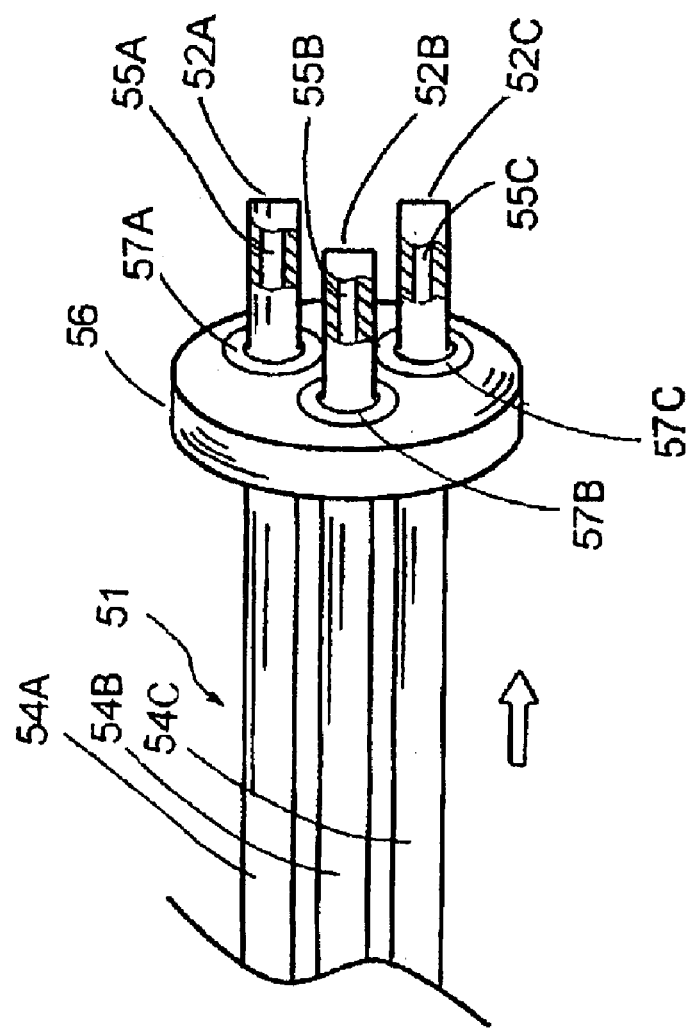
FIG. 5C is an embodiment of the coupling mechanism of the present invention comprising a gluing element for coupling the leaflets onto the medical catheter.

FIG. 5C shows an embodiment of the coupling mechanism of the present invention comprising a gluing element 51 with a plurality of gluing members 54A, 54B and 54C for coupling the leaflets onto the medical catheter 11. For example, each gluing member 54A, 54B or 54C passes through a restraining passageway 57A, 57B or 57C of a restraining support 56. Each gluing member, for example 54A, 54B or 54C, has a glue-supplying source 55A, 55B or 55C for providing biocompatible glue at a glue vent opening 52A, 52B or 52C. Other biocompatible adhesive or bonding agent may also be applicable.

Figure 6:
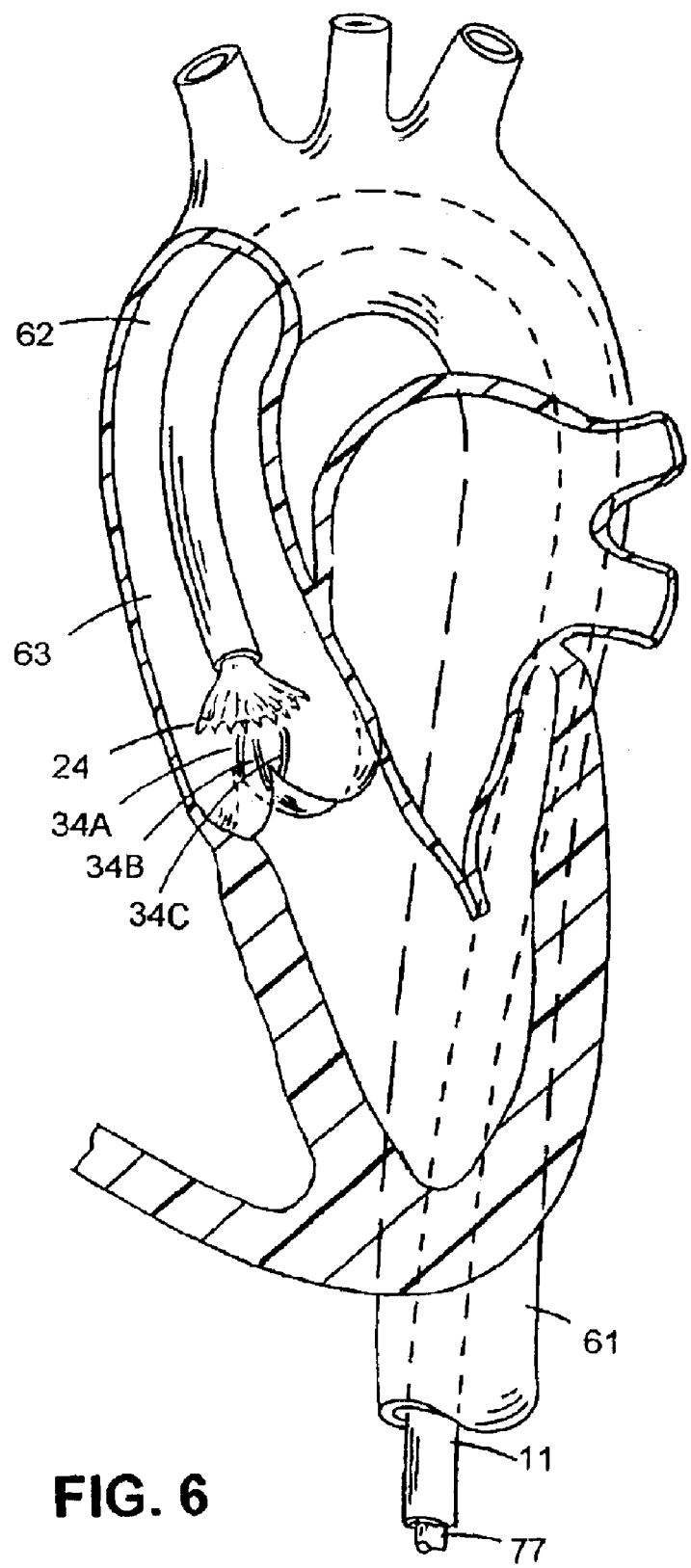
FIG. 6 is a perspective view for operating the medical catheter of the present invention in an illustrative example of the aortic valve removal.

FIG. 6 shows a perspective view for operating the medical catheter 11 of the present invention in an illustrative example of the aortic valve removal. A catheter 11 with a deployable inner catheter 77 is inserted endoluminally through the aorta 61. The catheter passes the aortic arch 62 into the ascending aorta 63. When approaching the anatomic site of the defective aortic valve, the coupling members 34A, 34B and/or 34C of the stapling mechanism 31 are deployed to couple and staple each leaflet. Upon stabilizing and immobilizing the leaflets, the cutting mechanism 24 is deployed at an appropriate self-expanding degree adapted for defining the valve base that is to be separated from the valve root. Then a cutting operation either by radiofrequency enhanced cutting or laser energized cutting is applied. The separated valve base along with its coupled leaflets can be removed out of a patient using a standard catheter-based removing procedure.

Briefly, heat is generated by supplying RF energy to at least one sharp-edge cutting member, which comprises a conductive contact end in contact with the valve base tissues. The RF energy can be applied to the conductive contact end(s) and consequently to the tissues. In a bipolar embodiment, a DIP (dispersive indifferent pad) type pad or electrode, that contacts the patient, is connected to the Indifferent Electrode Connector on a RF energy generator. Therefore, the RF energy delivery becomes effective when a close circuit from a RF generator through a patient and returning to the RF generator is formed. The generator should be grounded to avoid electrical interference. Heat is controlled by the power of the RF energy delivered, the delivery mode, and by the delivery duration. The standard RF energy generator means and its applications through conductive electrode means, to a patient are well known for those who are skilled in the art. A mono-polar radiofrequency procedure may also be applicable.

From the foregoing description, it should now be appreciated that a medical catheter and methods for removing a defective valve by immobilizing at least one valve leaflet of said defective valve and separating a valve base from a valve root of the defective valve, wherein the valve base comprises at least one commissure has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A medical catheter for removing a defective valve from a patient comprising: an elongate catheter shaft having a catheter distal end, a catheter distal section, a catheter proximal end, and at least a lumen between said catheter distal end and said catheter proximal end; a deployable inner catheter located within one of said at least a lumen; a coupling mechanism located at the catheter distal section configured to grip and immobilize a free edge of at least one valve leaflet of the defective valve; and an expandable and retractable cutting mechanism mounted at a distal end of the deployable inner catheter, wherein the cutting mechanism expands in diameter when the cutting member is positioned outside the catheter and retracts in diameter when positioned inside the catheter, and the cutting member is configured to cut and separate a valve base of said defective valve from a valve root of said defective valve.

2. The medical catheter according to claim 1, wherein the coupling mechanism comprises a stapling element configured to couple a free edge of said at least one valve leaflet onto said stapling element.

3. The medical catheter according to claim 1, wherein the coupling mechanism comprises a gripping element configured to couple a free edge of said at least one valve leaflet onto said gripping element.

4. The medical catheter according to claim 1, wherein the coupling mechanism comprises a gluing element configured to glue and bond a free edge of said at least one valve leaflet onto said gluing element.

5. The medical catheter according to claim 1, wherein the cutting mechanism comprises a sharp-edge element, and wherein a radiofrequency source is coupled to said sharp-edge element adapted for enhancing separation of the valve base of said defective valve.

6. The medical catheter according to claim 1, wherein the cutting mechanism comprises a fiber optic laser element, and wherein a laser energy source is coupled to said fiber optic laser element adapted for separating the valve base of said defective valve.

* * * * *